United States Patent
Akerele et al.

(10) Patent No.: US 11,000,470 B2
(45) Date of Patent: May 11, 2021

(54) METHODS, COMPOSITIONS, AND KITS FOR TREATING HAIR

(71) Applicant: L'OREAL, Paris (FR)

(72) Inventors: Dominic Akerele, New York, NY (US); Angela Park, Jersey City, NJ (US); Jaimie Mecca, Clifton, NJ (US); Kamini Patel, Iselin, NJ (US); Ivana Pur, New York, NY (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/665,147

(22) Filed: Jul. 31, 2017

(65) Prior Publication Data

US 2019/0029948 A1  Jan. 31, 2019

(51) Int. Cl.
| | |
|---|---|
| *A61K 8/92* | (2006.01) |
| *A61Q 5/00* | (2006.01) |
| *A61K 8/41* | (2006.01) |
| *A61K 8/73* | (2006.01) |
| *A61K 8/06* | (2006.01) |
| *A61Q 5/12* | (2006.01) |
| *A61Q 5/06* | (2006.01) |
| *A61K 8/81* | (2006.01) |

(52) U.S. Cl.
CPC ............. *A61K 8/922* (2013.01); *A61K 8/062* (2013.01); *A61K 8/416* (2013.01); *A61K 8/731* (2013.01); *A61K 8/8152* (2013.01); *A61Q 5/002* (2013.01); *A61Q 5/06* (2013.01); *A61Q 5/12* (2013.01); *A61K 2800/884* (2013.01)

(58) Field of Classification Search
CPC ...... A61K 8/922; A61K 8/8152; A61K 8/731; A61K 8/416; A61Q 5/002; A61Q 5/12
See application file for complete search history.

(56) References Cited

U.S. PATENT DOCUMENTS

| | | | | |
|---|---|---|---|---|
| 5,695,748 | A * | 12/1997 | Francis ................. | A61K 8/922 424/70.1 |
| 6,602,494 | B1 * | 8/2003 | Jahedshoar ............ | A61K 8/064 424/70.1 |
| 8,163,037 | B2 | 4/2012 | DeGeorge et al. | |
| 8,192,729 | B2 * | 6/2012 | Saute ...................... | A45D 7/06 424/70.12 |
| 8,722,029 | B2 | 5/2014 | Desenne et al. | |
| 8,905,049 | B2 | 12/2014 | Albert et al. | |
| 9,408,785 | B2 | 8/2016 | Pistorio et al. | |
| 2012/0204894 | A1 * | 8/2012 | Odoms .................. | A61K 8/375 132/202 |
| 2014/0261518 | A1 * | 9/2014 | Savaides ................. | A61Q 5/06 132/206 |
| 2016/0346172 | A1 | 12/2016 | Pistorio et al. | |

FOREIGN PATENT DOCUMENTS

WO     WO 0176543 A1 * 10/2001
WO     WO2016065439 A1    5/2016

* cited by examiner

*Primary Examiner* — Lakshmi S Channavajjala
(74) *Attorney, Agent, or Firm* — Polsinelli PC

(57) ABSTRACT

The present disclosure relates to methods, compositions, and kits for treating hair. The methods entail the use of multiple compositions, which can be incorporated into kits. The methods include: (I) optionally, cleansing the hair, for example, with a cleansing composition such as a shampoo; (II) optionally, treating the hair with a rinse-off conditioning mask, and rinsing the rinse-off conditioning mask from the hair; (III) applying a leave-on hair-treatment composition to the hair; (IV) without removing the leave-on hair-treatment composition, subsequently applying a leave-on hair crème to the hair; and (V) without removing the leave-on hair-treatment composition and the leave-on hair crème, styling the hair. The methods provide durable styling and conditioning benefits, frizz control/curl definition, and general hair manageability qualities.

50 Claims, No Drawings

METHODS, COMPOSITIONS, AND KITS FOR TREATING HAIR

FIELD OF THE DISCLOSURE

The present disclosure relates to methods, compositions, and kits for treating hair. The methods entail the use of multiple compositions, which can be incorporated into kits. The compositions are applied to the hair in a sequence to provide durable styling and conditioning benefits, curl definition, and general hair manageability and hair care qualities.

BACKGROUND

Individuals desire healthy and strong hair, as healthy looking hair is in general a sign of good health and good hair-care practices. Nonetheless, nutrition, environmental influences, and chemical hair treatments can lead to hair damage that significantly weakens and dulls the hair over time. Gloss and moisture balance are deleteriously affected making the hair more difficult to manage and style. Furthermore, dry hair that has been weakened or damaged is also prone to breakage and the formation of "split ends."

Nutrition plays a crucial role in the health of hair, but nutrition alone is not sufficient to compensate for the various types of physical, chemical, and environmental damage that prevent optimal hair quality. Physical hair damage is often the result of repeatedly manipulating the shape of the hair. For example, hair styles such as ponytails, buns, and braiding are quick and easy but when done too often and too tightly, can impart strain on the edges of the hair and cause a receding hair line. Hair also becomes physically damaged during detangling and styling. Excessive detangling can result in split ends and breakage.

Many chemical treatments are available for changing the appearance of hair. For example, hair may be lightened or bleached and oxidative dyes can be used to change the color of the hair. Chemical treatments for permanently straightening or curling the hair are also common. Chemical treatments are popular because their effects are long-lasting and can be drastic. Nonetheless, the biggest drawback to chemical treatments is the strain and damage they cause to the hair. This is because chemical treatments permanently change the chemical and physical structure of the hair. Another cause of chemical hair damage is heat. Repeated use of heating appliances such as flat irons and blow-dryers remove moisture from the surface of the hair cuticles, resulting in brittle, dry hair that become more vulnerable to breakage.

The environment also influences the health of hair. Regions with hard water can affect the look, feel and shine of the hair. This is because hard water leaves mineral deposits, which accumulate over time on the hair and eventually prevents moisture intake into the hair. The hair becomes dry, frizzy, and is prone to tangles. Environmental factors, such as strong sun, wind, cold air, extreme temperature variations and changes in air humidity can also damage the hair. The static and dry winter air contributes to moisture loss.

Dry and damaged hair can be particularly difficult to style, especially naturally curly hair. Individuals with naturally curly hair and chemically curly hair (from perming or waving) often seek to reduce frizz and improve curl definition, which becomes more difficult when the hair is damaged and dry. Naturally curly hair also tends to more easily tangle.

Thus, methods useful for treating hair including damaged and and/or naturally curly hair are desirable.

SUMMARY OF THE DISCLOSURE

The methods, compositions, and kits of the instant disclosure provide durable styling and conditioning benefits, impart frizz control and curl definition, and improve the health and manageability of the hair. After hair is optionally cleansed, for example, with a shampoo, a series of compositions are applied to the hair to impart a multitude of benefits to the hair. For example, the hair may be initially treated (after being optionally cleansed) with a rinse-off conditioning mask, which provides conditioning and detangling properties to the hair. After rinsing the rinse-off conditioning mask from the hair, a leave-on hair-treatment composition is applied to the hair. The leave-on hair-treatment composition provides additional conditioning and detangling properties, and improves curl definition and manageability. Without rinsing the leave-on-hair treatment composition from the hair, a leave-on hair crème is then applied to the hair. The leave-on hair crème provides long-lasting smoothness and styling benefits. These methods (or routines) are particularly useful for natural (non-chemically relaxed), curly African American hair, but are certainly not limited to this type of hair.

A typical method (also referred to as a "routine") for treating hair according to the instant disclosure includes:
  I. optionally, cleansing the hair, for example, with a cleansing composition such as a shampoo;
  II. optionally, treating the hair with a rinse-off conditioning mask, and rinsing the rinse-off conditioning mask from the hair after it has remained on the hair for a sufficient amount of time;
  III. applying a leave-on hair-treatment composition to the hair;
  IV. without removing the leave-on hair-treatment composition, applying a leave-on hair crème to the hair (to which the leave-on hair-treatment composition is already been applied); and
  V. without removing the leave-on hair-treatment composition and the leave-on hair crème, styling the hair.

The methods described above may be carried out once, or may be performed repeatedly, as needed, to attain a particular hair quality and style. For example, the method may be performed every day in conjunction with a daily bathing and/or cleansing routine. Likewise, the method may be performed every-other-day, once per week, twice per week, three times per week, four times per week, once per month, twice per month, etc.

A non-limiting example of a rinse-off conditioning mask that is useful in the methods include:
  (a) at least 4 wt. % of a natural fatty component, the natural fatty component comprising:
    (i) one or more solid or semi-solid natural fatty compounds having a melting point of 31° C. or higher; and
    (ii) one or more natural oils having a melting point below 31° C.;
      wherein the weight ratio of the one or more solid or semi-solid natural fatty compounds to the one or more natural oils is about 5:1 to about 1:5;
  (b) at least 1 wt. % of one or more cationic surfactants;
  (c) one or more nonionic thickening agents;
  (d) one or more emulsifiers;
  (e) one or more mineral based clays; and
  (f) water.

The rinse-off conditioning mask is unique in that it includes a high amount (at least 4 or 5 wt. %) of a natural fatty component. In particular, the natural fatty component includes both a natural solid or semi-solid fatty compound (e.g., a wax or butter) and a natural liquid oil. For example, a combination of Shea butter and sunflower seed oil can be particularly useful. An appropriate viscosity for the rinse-off mask may be attained instead using a natural fatty component, cationic surfactants, and nonionic thickening agents. For instance, nonionic polysaccharide thickening agents (e.g., sclerotium gum) can be particularly useful.

A non-limiting example of a leave-on hair-treatment composition that may be used in the methods include:
(a) at least 4 or at least 5 wt. % of a natural fatty component, the natural fatty component comprising:
    (i) one or more solid or semi-solid natural fatty compounds having a melting point of 31° C. or higher; and
    (ii) one or more natural oils having a melting point below 31° C.;
        wherein the weight ratio of the one or more solid or semi-solid natural fatty compounds to the one or more natural oils is about 5:1 to about 1:5;
(b) one or more cationic surfactants;
(c) one or more cellulose based thickening agents;
(d) one or more emulsifiers; and
(e) water.

The leave-on hair-treatment composition, like the rinse-off conditioning mask, includes a high amount (at least 4 or 5 wt. %) of a natural fatty component. The natural fatty component includes both a natural solid or semi-solid fatty compound (e.g., a wax or butter) and a natural liquid oil. For example, a combination of Shea butter and coconut oil can be particularly useful. An appropriate viscosity for the leave-on hair-treatment composition may be attained instead using a natural fatty component, cationic surfactants, and cellulose based thickening agents. For instance, hydroxypropyl methylcellulose can be particularly useful.

A non-limiting example of a leave-on hair crème includes:
(a) one or more natural oils;
(b) one or more water-soluble solvents;
(c) one or more acrylic- and/or acrylate-based polymers;
(d) one or more nonionic surfactants;
(e) optionally, one or more cationic polymers; and
(f) water;

The leave-on hair crème is typically "layered" onto the leave-on hair-treatment composition. In other words, the leave-on hair crème is applied to hair in which the leave-on hair-treatment composition has already been applied and not removed. The amount of natural oil(s) in the leave-in hair cream is high, for example, at least 4 or 5 wt. %. In some instances, soybean oil is particularly useful. In some cases, glycerin is a particularly useful water-soluble solvent that may be advantageously incorporated into the hair crème, for instance, in amounts of at least 4 or 5 wt. %.

The methods and compositions of the instant disclosure can be used at home as desired, for example, during an individual's regular shampooing bathing/showering routine, and therefore do not require special procedures that are only available at professional salons. Nonetheless, the methods may also be performed at salons. The compositions that are used in the methods may be provided in a kit. The kits typically include at least a leave-on hair-treatment composition and a leave-on hair crème. A rinse-off conditioning mask and/or a shampoo may also optionally be included in the kit. Each of the various compositions in the kit are typically separately contained, for example, contained in separate containers or contained in separate compartments of packaging. Instructions, mixing components, brushes, gloves, measuring tools, etc., may also optionally be included in the kits.

Finally, as mentioned previously, the hair-treatment compositions are unique in their ability to provide hair with improved manageability, long-lasting style and frizz control, and protection. Accordingly, the instant disclosure relates to methods for treating hair, for example, for improving the manageability of hair; for imparting lasting style, curl definition, and frizz control; for conditioning hair; for improving ease of combability and detangling of hair; and for styling the hair. The treatments and care of hair using the leave-on hair-treatment composition followed by a leave-on hair crème according to the methods of the instant disclosure may also eliminate the need to use a rinse-off conditioner after shampooing the hair, while at the same time, providing conditioning and styling benefits to the hair.

DETAILED DESCRIPTION OF THE DISCLOSURE

The methods disclosed herein relate to sequentially treating hair with a variety of compositions in a routine. The routines typically involve:
I. optionally, cleansing the hair, for example, with a cleansing composition such as a shampoo;
II. optionally, treating the hair with a rinse-off conditioning mask, and rinsing the rinse-off conditioning mask from the hair after it has remained on the hair for a sufficient amount of time;
III. applying a leave-on hair-treatment composition to the hair;
IV. without removing the leave-on hair-treatment composition, applying a leave-on hair crème to the hair (to which the leave-on hair-treatment composition has already been applied and not removed); and
V. without removing the leave-on hair-treatment composition and the leave-on hair crème, styling the hair.

The routine described above may be carried out once, or it may be performed repeatedly, as needed to attain a particular hair quality and style. For example, the routine may be performed every day in conjunction with a daily bathing and/or hair cleansing routine. Likewise, the routine may be performed every-other-day, once per week, twice per week, three times per week, four times per week, once per month, twice per month, etc. The routine may be carried out, for example, at home, by the consumer or may be performed at a salon by a professional stylist.

As noted above, the hair may be initially cleansed, for example, with a shampoo prior to further treatments in the routine. In some instances, it may be desirable to cleanse the hair with a sulfate-free shampoo.

After rinsing the shampoo from the hair, the hair may then optionally be treated with a rinse-off conditioning mask. Treating the hair with a rinse-off conditioning mask is useful in the routine for providing an added degree of conditioning, moisturizing, and detangling to the hair before subsequent application of a leave-on hair-treatment composition and a leave-on hair crème. As the term connotes, a "rinse-off conditioning mask" is rinsed from the hair. The rinse-off conditioning mask is typically rinsed from the hair shortly after it has been allowed to remain on the hair for a sufficient amount of time to carry out its intended purpose, e.g., to condition, moisturize, and provide detangling properties to the hair. For example, the rinse-off conditioning mask may be allowed to remain on the hair for about 30 seconds to about 30 minutes before being rinsed from the hair. In some cases, the rinse-off conditioning mask is allowed to remain on the hair for about 30 seconds to about 20 minutes, about 30 seconds to about 15 minutes, about 30 seconds to about 10 minutes, about 1 minute to about 30 minutes, about 1 minute to about 20 minutes, about 1 minute to about 15 minutes, about 1 minute to about 10 minutes, or about 2 minutes to about 8 minutes.

A leave-on hair-treatment composition is applied to the hair after the hair is optionally cleansed and after the hair is optionally treated with a rinse-off conditioning mask. The leave-on hair-treatment composition is typically applied to wet or damp hair, but may be applied to dry hair. As the term connotes, a "leave-on hair-treatment composition" is a composition that remains on the hair. The leave-on hair treatment composition is not rinsed from the hair prior to drying and styling the hair. The leave-on hair-treatment composition may be applied to the hair, for example, by first dispensing an amount of a hair-treatment composition into the hand(s) and by using the fingers to apply the leave-on hair-treatment composition throughout the hair, including from the base of the hair to the ends of the hair.

After a leave-on hair-treatment composition has been sufficiently applied to the hair, a leave-on hair crème is applied onto the hair, i.e., the leave-on hair crème is layered onto the hair. The term "layered" refers to applying a composition to hair to which another composition has already been applied. The term does not necessarily indicate that the compositions actually form separate layers on the hair—the second composition that is applied after a first composition may mix with the first composition on the hair. Additionally, as the term connotes, a "leave-on hair crème" is a composition that remains on the hair. The leave-on hair crème is not rinsed from the hair prior to drying and styling the hair.

The leave-on hair crème may be applied to the hair, for example, by first dispensing an amount of the leave-on hair crème into the hand(s) and by using the fingers to apply the leave-on hair crème throughout the hair, including from the base of the hair to the ends of the hair.

After application of the leave-on hair crème, the hair may be dried and styled. The hair may be allowed to dry naturally (e.g., without using any particular drying or heating device) or the hair may be subjected to drying and/or heating, for example, drying with a blow dryer.

Rinse-off conditioning masks according to the disclosure typically include:
 (a) at least 4 wt. % of a natural fatty component, the natural fatty component comprising:
  (i) one or more solid or semi-solid natural fatty compounds having a melting point of 31° C. or higher; and
  (ii) one or more natural oils having a melting point below 31° C.;
   wherein the weight ratio of the one or more solid or semi-solid natural fatty compounds to the one or more natural oils is about 5:1 to about 1:5;
 (b) at least 1 wt. % of one or more cationic surfactants;
 (c) one or more nonionic thickening agents;
 (d) one or more emulsifiers;
 (e) one or more mineral based clays, for example, one or more smectite clays; and
 (f) water.

The rinse-off conditioning mask includes a high amount (typically at least 4 or 5 wt. %) of a natural fatty component. The natural fatty component typically includes both a natural solid or semi-solid fatty compound (e.g., a wax or butter) and natural liquid oil. For purposes of the instant disclosure, a solid or semi-solid fatty compound is a fatty substance having a melting of 31° C. or higher. An oil, on the other hand, is a fatty substance having a melting point below 31° C. Accordingly, an oil will be a liquid at room temperature. Reference to a total amount of a natural fatty component does not necessarily indicate an absence of a non-natural fatty component in the rinse-off conditioning mask. In other words, in some cases, the rinse-off conditioning masks may include one or more non-natural fatty compounds in addition to the compounds of the natural fatty component. Nonetheless, it may be desirable to exclude non-natural fatty compounds in order to derive a natural product.

The term "natural" as used herein in the present disclosure refers to natural-based ingredients such as plant- or vegetable-derived ingredients, for example, the natural fatty component or the solid or semi-solid natural fatty compounds or the natural oils of the disclosure. The term "non-natural" as used herein in the present disclosure refers to ingredients that are not natural-based and may include alkane or hydrocarbon or synthetic oils such as mineral oil or silicone oil.

The total amount of natural fatty component is typically at least 4 or 5 wt. %, based on the total weight of the rinse-off conditioning mask. For example, the total amount of the natural fatty component in the rinse-off conditioning mask may be about 5 wt. % to about 25 wt. %, about 5 wt. %, to about 20 wt. %, about 5 wt. % to about 15 wt. %, or about 5 wt. % to about 10 wt. %, based on the total weight of the rinse-off conditioning mask.

Non-limiting examples of solid or semi-solid fatty compounds include those from plants, animals, and mineral sources, for example, Shea butter, bayberry wax, bees wax, illipe butter, paraffin wax, hard tallow, lanolin, kokum butter, Sal butter, spermaceti, murumuru seed butter, beeswax, ceresin wax, cocoa butter, jojoba wax, candelilla wax, palm butter, carnauba wax, esparto wax, shellac wax, sugarcane wax, lignite wax, ouricouri wax, rice bran wax, castor wax, Montan wax, sugar cane wax, rice bran wax, sunflower wax, and a mixture thereof. In some cases, Shea butter may be particularly useful.

The total amount of the one or more natural solid or semi-solid fatty compounds may vary but is typically about 1 to about 15 wt. %, based on the total weight of the rinse-off conditioning mask. In some cases, the total amount of the one or more natural solid or semi-solid fatty compounds is about 1 to about 10 wt. %, about 1 to about 8 wt. %, about 1 to about 6 wt. %, about 1 to about 4 wt. %, about 2 to about 15 wt. %, about 2 to about 10 wt. %, about 2 to about 8 wt. %, or about 2 to about 6 wt. %, based on the total weight of the rinse-off conditioning mask.

Non-limiting examples of natural oils include oils from plants, animals, and mineral sources, for example, coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a mixture thereof. In some cases, sunflower oil may be particularly useful.

The total amount of the one or more natural oils may vary but is typically about 1 to about 15 wt. %, based on the total weight of the rinse-off conditioning mask. In some cases, the total amount of the one or more natural oils is about 1 to about 10 wt. %, about 1 to about 8 wt. %, about 1 to about 6 wt. %, about 1 to about 4 wt. %, about 2 to about 15 wt.

%, about 2 to about 10 wt. %, about 2 to about 8 wt. %, or about 2 to about 6 wt. %, based on the total weight of the rinse-off conditioning mask.

The weight ratio of the one or more natural solid or semi-solid fatty compounds to the one or more natural oils may vary but is typically about 1:5 to about 5:1. In some cases the weight ratio of the one or more natural solid or semi-solid fatty compounds to the one or more natural oils is about 1:4 to about 4:1, about 1:3 to about 3:1, about 1:2 to about 2:1, or about 1:1.

Many cationic surfactants are known and may be used in the rinse-off conditioning masks. Non-limiting examples of cationic surfactants include cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyldiethylamine, arachidamidoethyldiethylamine, arachidamidoethyldimethylamine, quaternium-91, and a mixture thereof.

The total amount of the one or more cationic surfactant in the rinse-off conditioning mask may vary but it typically at least 1 wt. %, based on the total weight of the rinse-off conditioning mask. In some cases, the total amount of the one or more cationic surfactants may be about 1 wt. % to about 10 wt. %, about 1 wt. % to about 8 wt. %, about 1 wt. % to about 6 wt. %, about 1 wt. % to about 5 wt. %, about 2 wt. % to about 10 wt. %, about 2 wt. % to about 8 wt. %, about 2 wt. % to about 6 wt. %, or about 2 wt. % to about 5 wt. %.

The rinse-off conditioning mask typically includes one or more nonionic thickening agents. All thickening referred to throughout the disclosure may also be referred to as "rheology modifiers," "thickening compounds," "thickeners," "gelling agents," and the like. Nonionic thickening agents include nonionic guar gums, sclerotium gum, biopolysaccharide gums of microbial origin, gums derived from plant exudates, celluloses, in particular hydroxypropylcelluloses or hydroxyethylcelluloses, pectins, and mixtures thereof.

Among the nonionic thickening agents that may be mentioned are:

(1) celluloses modified with groups comprising at least one fatty chain; examples that may be mentioned include: hydroxyethylcelluloses modified with groups comprising at least one fatty chain, such as alkyl, arylalkyl or alkylaryl groups, or mixtures thereof, and in which the alkyl groups are preferably C8-C22, for instance the product NATROSOL PLUS GRADE 330 CS ($C_{16}$ alkyls) sold by the company Aqualon, or the product BERMOCOLL EHM 100 sold by the company Berol Nobel; and hydroxyethylcelluloses modified with alkylphenyl polyalkylene glycol ether groups, such as the product AMERCELL POLYMER HM-1500 (polyethylene glycol (15) nonylphenyl ether) sold by the company Amerchol, (2) hydroxypropyl guars modified with groups comprising at least one fatty chain, such as the product ESAFLOR HM 22 ($C_{22}$ alkyl chain) sold by the company Lamberti, and the products RE210-18 ($C_{14}$ alkyl chain) and RE205-1 ($C_{20}$ alkyl chain) sold by the company Rhone-Poulenc, (3) copolymers of vinylpyrrolidone and of fatty-chain hydrophobic monomers; examples that may be mentioned include: the products ANTARON V216 or GANEX V216 (vinylpyrrolidone/hexadecene copolymer) sold by the company I.S.P. the products ANTARON V220 or GANEX V220 (vinylpyrrolidone/eicosene copolymer) sold by the company I.S.P., (4) copolymers of $C_1$-$C_6$ alkyl methacrylates or acrylates and of amphiphilic monomers comprising at least one fatty chain, for instance the oxyethylenated methyl acrylate/stearyl acrylate copolymer sold by the company Goldschmidt under the name ANTIL 208, (5) copolymers of hydrophilic methacrylates or acrylates and of hydrophobic monomers comprising at least one fatty chain, for instance the polyethylene glycol methacrylate/lauryl methacrylate copolymer, (6) polyurethane polyethers comprising in their chain both hydrophilic blocks usually of polyoxyethylenated nature and hydrophobic blocks, which may be aliphatic sequences alone and/or cycloaliphatic and/or aromatic sequences, (7) polymers with an aminoplast ether backbone containing at least one fatty chain, such as the PURE THIX compounds sold by the company Sud-Chemie.

In some instances, the nonionic thickening agents are chosen from the group consisting of polysaccharides and associative polymers. In some cases, the preferred nonionic thickening agents are sclerotium gum, guar gums, hydroxyalkyl celluloses optionally modified with a hydrophobic group, such as hydroxyethylcelluloses, hydroxymethylcelluloses optionally modified with a hydrophobic group, and inulins optionally modified with a hydrophobic group. In some cases, sclerotium gum is particularly useful. Anionic thickening agents such as xanthan gum, may be excluded from the rinse-off conditioning mask compositions. In other words, the rinse-off condition mask may be free or essentially free of anionic thickening agents, including xanthan gum.

The total amount of the one or more nonionic thickening agents may vary but is typically about 0.1 to about 8 wt. % based on the total weight of the rinse-off conditioning mask. In some cases, the total amount of the one or more nonionic thickening agents is about 0.1 to about 6 wt. %, about 0.1 to about 5 wt. %, about 0.2 to about 8 wt. %, about 0.2 to about 6 wt. %, about 0.2 to about 5 wt. %, based on the total weight of the rinse-off conditioning mask.

The rinse-off conditioning masks are typically in the form of an emulsion, for example, a water-in-oil emulsion. Accordingly, one or more emulsifiers are usually included. Useful emulsifiers include, for example, fatty acids, fatty alcohols, esters of polyols and of a fatty acid, polyol fatty esters and fatty ethers with a branched or unsaturated chain containing from 10 to 30 carbon atoms, esters of sorbitan and of a fatty acids, esters of sugar and of a fatty acid, and a mixture thereof. The fatty chains in the emulsifiers may be, for example from about 8 to about 35 carbon atoms in length, and may be saturated or unsaturated, and may be optionally branched. In some cases, the fatty chains are about 10 to about 30 carbon atoms in length or about 12 to about 24 carbon atoms in length.

Non-limiting examples of emulsifiers include sorbitan laurate, sorbitan palmitate, sorbitan sesquiisostearate, sorbitan sesquioleate, sorbitan sesquistearate, sorbitan stearate, sorbitan oleate, sorbitan monoisostearate, sorbitan tristearate, sorbitan trioleate, sorbitan tristearate; glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate; polyglyceryl-4 isostearate, polyglyceryl-3 oleate, polyglyceryl-2 sesquioleate, triglyceryl diisostearate, diglyceryl monooleate, tetraglyceryl monooleate, glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, sucrose cocoate, sucrose laurate, methyl glucose sesquistearate, methyl glucose dioleate, cetyl alcohol, stearyl alcohol, cetearyl alcohol, cetyl esters, and a mixture thereof, The total amount of the one or more emulsifiers may vary depending on the other components and their amounts in the rinse-off conditioning mask. Nonetheless, the total amount of the one or more emulsifiers is typically about 0.5 to about 20 wt. %, based on the total weight of the rinse-off conditioning mask. In some instances, the total amount of the one or more emulsifiers may be about 1 to about 20 wt. %, about 1 to about 15 wt. %, about 1 to about 12 wt. %, about 1 to about 10 wt. %, about 2 to about 20 wt. %, about 2 to about 15 wt. %, about 2 to about 12 wt. %, about 2 to about 10 wt. %, about 5 to about 20 wt. %, about 5 to about 15 wt. %, about 5 to about 12 wt. %, or about 5 to about 10 wt. %, based on the total weight of the rinse-off conditioning mask.

One or more mineral based clays are typically included in the rinse-off conditioning masks. Mineral based clays are sometimes classified as 1:1 or 2:1, this originates because they are fundamentally built of tetrahedral silicate sheets and octahedral hydroxide sheets. A 1:1 clay includes one tetrahedral sheet and one octahedral sheet. Examples include kaolinite and serpentine. A 2:1 clay includes an octahedral sheet sandwiched between two tetrahedral sheets, and examples are talc, vermiculite and montmorillonite. Mineral based clays include: kaolins (e.g., the minerals kaolinite, dickite, halloysite, and nacrite); smectites, (e.g., dioctahedral smectites such as montmorillonite, nontronite and beidellite and trioctahedral smectites for example saponite); Illites (e.g., clay-micas); chlorites; and other 2:1 clay types such as sepiolite and attapulgite.

In some instances, the rinse-off conditioning masks include a kaolinite and/or a smectite clays. Kaolinites, of formula $Al_2Si_2O_5(OH)_4$, are clay minerals of 1:1 type (which means that a sheet of kaolinite is formed of two layers: a tetrahedral layer $SiO_4$/an octahedral layer $Al(OH^-)_5$ O) characterized by low cation exchange with the exception of $Fe^{3+}$ (x=0). The group of kaolinites includes dickite and nacrite which are kaolinites characterized by different stacking of the same layers. Smectites are clays characterized by the presence of interlayer water and low cationic charge (x=0.2-0.6). They may comprise different exchangeable cations. A distinction is made between the dioctahedral smectites which include montmorillonite, beidellite and nontronite, trioctahedral smectites which include saponite, hectorite, stevensite, sauconite and talc. In some instances, preference is given to the use of a trioctahedral smectite which, in addition to silicon and magnesium, contains sodium such as stevensite, hectorite or saponite. Finally, in some cases, preference is given to the clay ghassoul or "rhassoul", which is a clay with natural saponins found in Morocco containing at least 90% stevensite and identified under the INCI name as "Moroccan Lava Clay."

The total amount of mineral based clay in the rinse-off conditioning mask may vary, but is typically about 0.1 to about 10 wt. %, based on the total weight of the rinse-off conditioning mask. In some cases, the total amount of the mineral based clay is about 0.1 to about 8 wt. %, about 0.1 to about 6 wt. %, about 0.1 to about 5 wt. %, about 0.2 to about 10 wt. %, about 0.2 to about 8 wt. %, about 0.2 to about 6 wt. %, about 0.2 to about 5 wt. %, or about 0.2 to about 3 wt. %, based on the total weight of the rinse-off conditioning mask.

The total amount of water in the rinse-off conditioning mask may vary but is typically about 50 to about 90 wt. %, based on the total weight of the rinse-off conditioning mask. In some cases, the total amount of water is about 60 to about 90 wt. %, about 50 to about 80 wt. %, or about 60 to about 80 wt. %, based on the total weight of the rinse-off conditioning mask.

Water-soluble solvents may optionally be included in the rinse-off conditioning mask. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%. Non-limiting examples of water-soluble solvents include, for example, organic solvents, such as $C_{1-4}$ alcohols, polyols, glycols, and a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents are chosen from polyols which include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof. Polyhydric alcohols are useful.

Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some cases, the water-soluble solvent may be selected from the group consisting of one or more glycols, $C_{1-4}$ alcohols, polyols, and a mixture thereof. In some cases, the water-soluble solvent is selected from the group consisting of hexylene glycol, propylene glycol, caprylyl glycol, glycerin, ethanol, isopropyl alcohol, and a mixture thereof.

The total amount of the one or more water-soluble solvents may vary but is typically about 0.1 to about 25 wt. %, based on the total weight of the rinse-off conditioning mask. In some cases, the total amount of the one or more water-soluble solvents may be about 0.1 to about 20 wt. %, about 0.1 to about 15 wt. %, about 0.1 to about 10 wt. %, about 0.1 to about 5 wt. %, about 0.5 to about 20 wt. %, about 0.5 to about 15 wt. %, about 0.5 to about 10 wt. %, or about 0.5 to about 5 wt. %, based on the total weight of the rinse-off conditioning mask.

The rinse-off conditioning masks of the instant disclosure do not require alkoxylated compounds, for example, ethoxylated thickeners and/or ethoxylated surfactants nor do the conditioning masks require sulfates, such as sulfate surfactants. An appropriate viscosity for the rinse-off mask may be attained using a natural fatty component, cationic surfactants, and thickening agents.

A non-limiting embodiment of a rinse-off conditioning mask according to the disclosure relates to a water-in-oil emulsion comprising:
  (a) about 4 to about 15 wt. %, about 5 to about 12 wt. %, or at least 5 to about 10 wt. % of a natural fatty component, the natural fatty component comprising:
    (i) about 1 to about 8 wt. %, about 1 to about 6 wt. %, or about 1 to about 5 wt. % of one or more solid or semi-solid natural fatty compounds having a melting point of 31° C. or higher, for example, Shea butter; and
    (ii) about 1 to about 8 wt. %, about 1 to about 6 wt. %, or about 1 to about 5 wt. % of one or more natural oils having a melting point below 31° C., for example, sunflower seed oil;
      wherein the weight ratio of (i) to (ii) is about 4:1 to about 4:1, about 3:1 to about 1:3, or about 2:1 to about 1:2;
  (b) at least 1 to about 10 wt. %, at least 1 to about 8 wt. %, or about 2 to about 5 wt. % of one or more cationic surfactants, for example, behentrimonium chloride;
  (c) about 0.1 to about 8 wt. %, about 0.1 to about 6 wt. %, or about 0.2 to about 5 wt. % of one or more nonionic thickening agents, for example, sclerotium gum;
  (d) about 1 to about 20 wt. %, about 1 to about 15 wt. %, or about 2 to about 10 wt. % of one or more emulsifiers;
  (e) about 0.1 to about 5 wt. % of a smectite clay;
  (f) about 50 to about 90 wt. %, about 55 to about 85 wt. %, or about 60 to about 80 wt. % of water; and
  (e) optionally, about 0.1 to about 10 wt. %, about 0.1 to about 5 wt. %, or about 0.5 to about 5 wt. % one or more water-soluble solvents, for example, one or more glycols and/or one or more alcohols (e.g., isopropyl alcohol).

The natural solid or semi-solid fatty compounds, the natural oils, the cationic surfactants, the polysaccharide thickeners, the emulsifiers, and the water-soluble solvents useful for the above embodiment are the same as those described previously.

Leave-on hair treatment compositions according to the instant disclosure typically include:
  (a) at least 4 wt. % of a natural fatty component, the natural fatty component comprising:
    (i) one or more solid or semi-solid natural fatty compounds having a melting point of 31° C. or higher; and
    (ii) one or more natural oils having a melting point below 31° C.;
      wherein the weight ratio of the one or more solid or semi-solid natural fatty compounds to the one or more natural oils is about 5:1 to about 1:5;
  (b) one or more cationic surfactants;
  (c) one or more cellulose based thickening agents;
  (d) one or more emulsifiers; and
  (e) water.

The leave-on hair-treatment compositions, like the rinse-off conditioning mask, include a high amount (at least 4 or 5 wt. %) of a natural fatty component. The natural fatty component typically includes both a natural solid or semi-solid fatty compound (e.g., a wax or butter) and natural liquid oil. Reference to a total amount of a natural fatty component does not necessarily connote an absence of a non-natural fatty component. In other words, in some cases, leave-on hair-treatment compositions may include one or more non-natural fatty compounds in addition to the natural fatty component. Nonetheless, it may be desirable to exclude non-natural fatty compounds in order to derive a natural product.

The total amount of natural fatty component is typically at least 4 or at least 5 wt. %, based on the total weight of the leave-on hair treatment composition. For example, the total amount of the natural fatty component in the leave-on hair-treatment compositions may be about 5 wt. %, to about 25 wt. %, about 5 wt. %, to about 20 wt. %, about 5 wt. % to about 15 wt. %, or about 5 wt. % to about 10 wt. %, based on the total weight of the leave-on hair treatment composition.

Non-limiting examples of solid or semi-solid fatty compounds include those from plants, animals, and mineral sources, for example, Shea butter, bayberry wax, bees wax, illipe butter, paraffin wax, hard tallow, lanolin, kokum butter, Sal butter, spermaceti, murumuru seed butter, beeswax, ceresin wax, cocoa butter, jojoba wax, candelilla wax, palm butter, carnauba wax, esparto wax, shellac wax, sugarcane wax, lignite wax, ouricouri wax, rice bran wax, castor wax, Montan wax, sugar cane wax, rice bran wax, sunflower wax, and a mixture thereof. In some cases, Shea butter may be particularly useful.

The total amount of the one or more natural solid or semi-solid fatty compounds may vary but is typically about 1 to about 15 wt. %, based on the total weight of the leave-on hair treatment composition. In some cases, the total amount of the one or more natural solid or semi-solid fatty compounds is about 1 to about 10 wt. %, about 1 to about 8 wt. %, about 1 to about 6 wt. %, about 1 to about 4 wt. %, about 2 to about 15 wt. %, about 2 to about 10 wt. %, about 2 to about 8 wt. %, or about 2 to about 6 wt. %, based on the total weight of the leave-on hair treatment composition.

Non-limiting examples of natural oils include oils from plants, animals, and mineral sources, for example, coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a mixture thereof. In some cases, coconut oil may be particularly useful.

The total amount of the one or more natural oils may vary but is typically about 1 to about 15 wt. %, based on the total weight of the leave-on hair treatment composition. In some cases, the total amount of the one or more natural oils is about 1 to about 10 wt. %, about 1 to about 8 wt. %, about 1 to about 6 wt. %, about 1 to about 4 wt. %, about 2 to about 15 wt. %, about 2 to about 10 wt. %, about 2 to about 8 wt. %, or about 2 to about 6 wt. %, based on the total weight of the leave-on hair treatment composition.

The weight ratio of the one or more natural solid or semi-solid fatty compounds to the one or more natural oils may vary but is typically about 1:5 to about 5:1. In some cases the weight ratio of the one or more natural solid or semi-solid fatty compounds to the one or more natural oils is about 1:4 to about 4:1, about 1:3 to about 3:1, about 1:2 to about 2:1, or about 1:1.

Many cationic surfactants are known and may be used in the leave-on hair treatment composition. Non-limiting examples of cationic surfactants include cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, stearamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyldiethylamine, arachidamidoethyldiethylamine, arachidamidoethyldimethylamine, quaternium-91, and a mixture thereof.

The total amount of the one or more cationic surfactant in the leave-on hair treatment composition may vary but it typically about 0.1 to about 10 wt. %, based on the total weight of leave-on hair treatment composition. In some cases, the total amount of the one or more cationic surfactants may be about 0.1 wt. % to about 8 wt. %, about 0.1 wt. % to about 6 wt. %, about 0.1 wt. % to about 5 wt. %, about 0.5 wt. % to about 10 wt. %, about 0.5 wt. % to about 8 wt. %, about 0.5 wt. % to about 6 wt. %, about 0.5 wt. % to about 5 wt. %, or about 0.5 wt. % to about 4 wt. %, based on the total weight of the leave-on hair-treatment composition.

The leave-on hair treatment composition typically includes one or more cellulose based thickening agents. Non-limiting examples of cellulose based thickening agent include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and a mixtures thereof. In some instances hydroxypropyl methylcellulose is particularly useful.

Additional thickening agents (non-cellulose based thickening agents), for example, nonionic thickening agents that are non-cellulose-based may also optionally be included in the leave-on hair treatment compositions. In some cases, a polysaccharide thickening agent that is non-cellulose-based may be useful (e.g., starches, vegetable gums, and pectin). Non-limiting examples of such polysaccharide thickening agents include sclerotium gum, cellulose, diutan gum, carrageenan, gellan gum, welan gum, pectin, starch, galactoarabinan, alginate, and a mixture thereof. In some instances, sclerotium gum may be particularly useful. Furthermore, in some instances a combination of sclerotium gum and hydroxypropyl methylcellulose may be particularly useful. Anionic thickening agent such as xanthan gum may be excluded from the leave-on hair treatment compositions. In other words, the leave-on hair treatment compositions may be free or essentially free of anionic thickening agents including xanthan gum.

The total amount of the one or more cellulose-based thickening agents may vary but is typically about 0.1 to about 8 wt. % based on the total weight of the leave-on hair treatment composition. In some cases, the total amount of the one or more cellulose-based thickening agents is about 0.1 to about 6 wt. %, about 0.1 to about 5 wt. %, about 0.2 to about 8 wt. %, about 0.2 to about 6 wt. %, about 0.2 to about 5 wt. %, based on the total weight of the leave-on hair treatment composition.

The leave-on hair treatment compositions are typically in the form of an emulsion, for example, a water-in-oil emulsion. Accordingly, one or more emulsifiers are usually included. Useful emulsifiers include, for example, fatty acids, fatty alcohols, esters of polyols and of a fatty acid, polyol fatty esters and fatty ethers with a branched or unsaturated chain containing from 10 to 30 carbon atoms, esters of sorbitan and of fatty acids, esters of sugar and of a fatty acid, and a mixture thereof. The fatty chains in the emulsifiers may be, for example from about 8 to about 35 carbon atoms in length, and may be saturated or unsaturated, and may be optionally branched. In some cases, the fatty chains are about 10 to about 30 carbon atoms in length or about 12 to about 24 carbon atoms in length.

Non-limiting examples of emulsifiers include sorbitan laurate, sorbitan palmitate, sorbitan sesquiisostearate, sorbitan sesquioleate, sorbitan sesquistearate, sorbitan stearate, sorbitan oleate, sorbitan monoisostearate, sorbitan trisostearate, sorbitan trioleate, sorbitan tristearate; glyceryl behenate, glyceryl caprate, glyceryl caprylate, glyceryl caprylate/caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate; polyglyceryl-4 isostearate, polyglyceryl-3 oleate, polyglyceryl-2 sesquioleate, triglyceryl diisostearate, diglyceryl monooleate, tetraglyceryl monooleate, glycol distearate, glycol hydroxystearate, glycol oleate, glycol ricinoleate, glycol stearate, propylene glycol isostearate, propylene glycol hydroxystearate, propylene glycol laurate, propylene glycol myristate, propylene glycol oleate, propylene glycol ricinoleate, propylene glycol stearate, sucrose cocoate, sucrose laurate, methyl glucose sesquistearate, methyl glucose dioleate, cetyl alcohol, stearyl alcohol, cetearyl alcohol, cetyl esters, and a mixture thereof. In some instances cetyl esters may be particularly useful. Likewise, in some cases, cetearyl alcohol may be particularly useful. Furthermore, in some cases, a combination of cetyl esters and cetearyl alcohol may be particularly useful.

The total amount of the one or more emulsifiers may vary depending on the other components and their amounts in the leave-on hair treatment composition. Nonetheless, the total amount of the one or more emulsifiers is typically about 0.5 to about 20 wt. %, based on the total weight of the leave-on hair treatment composition. In some instances, the total amount of the one or more emulsifiers may be about 1 to about 20 wt. %, about 1 to about 15 wt. %, about 1 to about 12 wt. %, about 1 to about 10 wt. %, about 2 to about 20 wt. %, about 2 to about 15 wt. %, about 2 to about 12 wt. %, about 2 to about 10 wt. %, about 5 to about 20 wt. %, about 5 to about 15 wt. %, about 5 to about 12 wt. %, or about 5 to about 10 wt. %, based on the total weight of the leave-on hair treatment composition.

The total amount of water in the leave-on hair treatment compositions may vary but is typically about 50 to about 92 wt. %, based on the total weight of the leave-on hair treatment compositions. In some cases, the total amount of water is about 60 to about 90 wt. %, about 50 to about 80 wt. %, or about 60 to about 80 wt. %, based on the total weight of the leave-on hair treatment composition.

Water-soluble solvents may optionally be included in the leave-on hair treatment compositions. Non-limiting examples of water-soluble solvents include, for example, organic solvents, such as $C_{1-4}$ alcohols, polyols, glycols, and a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents are chosen from polyols which include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof. Polyhydric alcohols are useful.

Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some cases, the water-soluble solvent may be selected from the group consisting of one or more glycols, $C_{1-4}$ alcohols, polyols, and a mixture thereof. In some cases, the water-soluble solvent is selected from the group consisting of hexylene glycol, propylene glycol, caprylyl glycol, glycerin, ethanol, isopropyl alcohol, and a mixture thereof.

The total amount of the one or more water-soluble solvents may vary but is typically about 0.1 to about 25 wt. %, based on the total weight of the leave-on hair treatment composition. In some cases, the total amount of the one or more water-soluble solvents may be about 0.1 to about 20 wt. %, about 0.1 to about 15 wt. %, about 0.1 to about 10 wt. %, about 0.5 to about 20 wt. %, about 0.5 to about 15 wt. %, about 0.5 to about 10 wt. %, about 2 to about 20 wt. %, about 2 to about 15 wt. %, ab out 5 to about 20 wt. %, or about 5 to about 15 wt. %, based on the total weight of the leave-on hair treatment compositions.

The leave-on hair treatment compositions of the instant disclosure do not require alkoxylated compounds, for example, ethoxylated thickeners and/or surfactants nor does the conditioning mask require sulfates, such as sulfate surfactants. An appropriate viscosity for the leave-on hair treatment composition is attained instead using a natural fatty component, cationic surfactants, and thickening agents.

A non-limiting embodiment of a leave-on hair-treatment composition according to the disclosure relates to a water-in-oil emulsion comprising:
(a) at least 4 wt. % to about 15 wt. %, at least 5 wt. % to about 12 wt. %, or at least 5 wt. % to about 10 wt. % of a natural fatty component, the natural fatty component comprising:
  (i) about 1 to about 10 wt. %, about 1 to about 8 wt. %, or about 2 to about 6 wt. % of one or more solid or semi-solid natural fatty compounds having a melting point of 31° C. or higher, for example, Shea butter; and
  (ii) about 1 to about 10 wt. %, about 1 to about 8 wt. %, or about 2 to about 6 wt. % of one or more natural oils having a melting point below 31° C., for example, coconut oil;
  wherein the weight ratio of (i) to (ii) is about 2:1 to about 1:2;
(b) about 0.1 to about 10 wt. %, about 0.1 to about 6 wt. %, or about 0.5 to about 5 wt. % of one or more cationic surfactants, for example, behentrimonium chloride;
(c) about 0.1 to about 10 wt. %, about 0.1 to about 8 wt. %, or about 0.5 to about 5 wt. % of one or more cellulose based thickening agents, for example, hydroxypropyl methyllcellulose;
(d) about 1 to about 20 wt. %, about 1 to about 15 wt. %, or about 2 to about 10 wt. % of one or more emulsifiers;
(e) about 50 to about 90, about 60 to about 90, or about 65 to about 80 wt. % of water; and (f) optionally, about 1 to about 20 wt. %, about 1 to about 15 wt. %, or about 5 to about 10 wt. % one or more water-soluble solvents, for example, one or more glycols, glycerin, one or more alcohols, and a mixture thereof.

The natural solid or semi-solid fatty compounds, the natural oils, the cationic surfactants, the cellulose based thickeners, the emulsifiers, and the water-soluble solvents useful for the above embodiment are the same as those described previously.

Leave-on hair crème compositions according to the instant disclosure typically include:

(a) one or more natural oils;
(b) one or more water-soluble solvents;
(c) one or more acrylic- and/or acrylate-based polymers;
(d) one or more nonionic surfactants;
(e) optionally, one or more cationic polymers; and
(f) water;

The leave-on hair crème typically has a "creamy" texture/viscosity, due in part to the inclusion of the one or more acrylic- and/or acrylate-based polymers. These types of polymers can provide a gel/cream-like consistency with viscoelastic properties.

Non-limiting examples of natural oils include oils from plants, animals, and mineral sources, for example, coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a mixture thereof. In some cases, soybean oil may be particularly useful.

The total amount of the one or more natural oils may vary but is typically about 1 to about 30 wt. %, based on the total weight of the leave-on hair crème. In some cases, the total amount of the one or more natural oils is about 1 to about 25 wt. %, about 1 to about 20 wt. %, about 1 to about 15 wt. %, about 1 to about 10 wt. %, about 2 to about 30 wt. %, about 2 to about 25 wt. %, about 2 to about 20 wt. %, about 2 to about 15 wt. %, about 2 to about 10 wt. %, about 5 to about 30 wt. %, about 5 to about 25 wt. %, about 5 to about 20 wt. %, or about 5 to about 15 wt. %, based on the total weight of the leave-on hair-crème.

Water-soluble solvents include, for example, glycerin, $C_{1-4}$ alcohols, organic solvents, polyols, glycols, and a mixture thereof. As examples of organic solvents, non-limiting mentions can be made of monoalcohols, such as ethyl alcohol, isopropyl alcohol, propyl alcohol, benzyl alcohol, and phenylethyl alcohol. Other suitable examples organic solvents areglycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Yet other suitable examples of organic solvents are glycols, and polyols such as ethylene glycol, propylene glycol, butylene glycol, hexylene glycol, propane diol, and glycerin. The organic solvents can be volatile or non-volatile compounds.

Further non-limiting examples of water-soluble solvents are chosen from polyols, including alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Other examples of polyols or polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some cases, the water-soluble solvent may be selected from the group consisting of one or more glycols, $C_{1-4}$ alcohols, polyols, and a mixture thereof. In some cases, the water-soluble solvent is selected from the group consisting of hexylene glycol, propylene glycol, caprylyl glycol, glycerin, ethanol, isopropyl alcohol, and a mixture thereof.

The total amount of the one or more water-soluble solvents may vary but is typically about 1 to about 50 wt. %, based on the total weight of the leave-on hair crème. In some cases, the total amount of the one or more water-soluble solvents may be about 1 to about 40 wt. %, about 1 to about 30 wt. %, about 5 to about 50 wt. %, about 5 to about 40 wt. %, or about 5 to about 30 wt. %, or about 10 to about 25 wt. %, based on the total weight of the leave-on hair crème.

In some instances, the leave-on hair crème includes glycerin. The total amount of glycerin may vary but is typically in an amount of about 1 to about 40 wt. %, based on the total weight of the leave-on hair crème. In some cases, the total amount of glycerin may be about 1 to about 35 wt. %, about 1 to about 30 wt. %, about 1 to 25 wt. %, about 5 to about 40 wt. %, about 5 to about 35 wt. %, about 5 to about 30 wt. %, or about 5 to about 25 wt. %, or about 10 to about 30 wt. %, or about 7 to about 25 wt. %, or about 10 to about 25 wt. %, or about 10 to about 20 wt. %, based on the total weight of the leave-on hair crème. Without being limited to any one theory, it is believed by the inventors of the present invention that the combination of glycerin with soybean oil in the leave-on hair crème provides long-lasting smoothness and shine to the hair.

Acrylic- and/or acrylate-based polymers include, but are not limited to, polymers based on acrylic acid crosslinked with an allyl ether of pentaerythritol, or an allyl ether of sucrose, or an allyl ether of propylene. Such polymers are also known as gelling agents and are generally of high molecular weight. Variations of such copolymers are also termed carbomers. The carbomers may have high molecular weights ranging from about 700,000 to about 5,000,000.

Acrylic- and/or acrylate-based polymers include carbomers which are commercially available under the tradename CARBOPOL from the supplier, Lubrizol, examples of which are CARBOPOL 934, 940, 941, 951, 954, 956, 980, 981, 1342, 2984, CARBOMER EDT 2001, CARBOMER-934P, and CARBOMER ULTREZ 10. Carbomers may also be commercially available under the tradename TEGO CARBOMER from the supplier, Evonik Industries, examples of which are TEGO CARBOMER 134, 140, 141, and 340 FD.

One particularly acrylic- and/or acrylate-based polymers is a carbomer known under the tradename, CARBOPOL 980 (company Lubrizol).

Acrylic- and/or acrylate-based polymers also include copolymers of two or more monomers consisting of acrylic acid, methacrylic acid or one of their simple esters. Suitable examples of a copolymer of two or more monomers consisting of acrylic acid, methacrylic acid or one of their simple esters, include, but are not limited to, acrylates copolymers.

Acrylic- and/or acrylate-based polymers may also be chosen from a copolymer of the ester of methacrylic acid and the polyethylene glycol ether of a C12-C22 fatty alcohol, and one or more monomers of acrylic acid, methacrylic acid, or one of their simple esters.

Suitable examples of a copolymer of the ester of methacrylic acid and the polyethylene glycol ether of a C12-C22 fatty alcohol, and one or more monomers of acrylic acid, methacrylic acid, or one of their simple esters, include, but are not limited to, Acrylates/Beheneth-25 Methacrylate Copolymer and Acrylates/Steareth-20 Methacrylate Copolymer. Other examples are ethyl acrylates/methyl methacrylates copolymer emulsion (chemical name) (INCI name: water (and) acrylates copolymer), which is commercially available from Daito Kasei Kogyo Co., Ltd., under the trade name DAITOSOL 5000AD. This product is sold in the form of an emulsion that contains water, ethyl acrylates/methyl methacrylates copolymer, sodium dehydroacetate, and laureth-21. Another suitable acrylates copolymer is ethyl methacrylates/N-butyl acrylates/2-methylhexyl acrylates copolymer emulsion (chemical name) (INCI name: water (and) acrylates/ethylhexyl acrylates copolymer), which is also commercially available from Daito Kasei Kogyo Co., Ltd., under the trade name DAITOSOL 5000SJ. This product is sold in the form of an emulsion that contains water, ethyl methacrylates/N-butyl acrylates/2-methylhexyl acrylates copolymer, and Laureth-20.

Other acrylates copolymers include an alkyl (meth)acrylates copolymer emulsion (INCI name: acrylates copolymer), which is commercially available from Nippon LSC Ltd., under the trade name YODOSOL GH34F; a styrene/acrylates copolymer emulsion (INCI name), which is commercially available from Nippon LSC Ltd., under the tradename YODOSOL GH41F; a styrene/acrylates copolymer emulsion (INCI name), and which is commercially available from BASF under the tradename JONCRYL 77 (which contains the copolymer in the form of an ammonia salt, along with water and polypropylene glycol); a Polyacrylates-21 (and) acrylates/dimethylaminoethyl methacrylates copolymer (INCI name), commercially available from Interpolymer under the tradename SYNTRAN PC5100, the chemical composition of which includes, in addition to water and the two acrylates copolymers having CAS Nos. 68541-61-7 and 67380-24-9 respectively, ethoxylated secondary alcohol (CAS No. 84133-50-6) and sodium laurylpolyethoxyethanol sulfate (CAS No. 68891-38-3); a styrene/acrylates/ammonium methacrylates copolymer (and) butylene glycol (and) sodium Laureth-12 sulfate (INCI name), commercially available from Interpolymer under the tradename Syntran® 5760 as a 40 percent aqueous dispersion; and a polyurethane-10 and PEG-12 dimethicone alcohol copolymer emulsion (INCI name), commercially available from Nippon LSC under the tradename Yodosol PUD (which also includes ethanol, 2-phenoyl-ethanol, and water in the emulsion). Acrylic-based polymeric compounds also include acrylates copolymers such as those commercially available from the company Rohm & Haas under the tradename, ACULYN 33.

Other acrylic- and/or acrylate-based polymers include copolymers of the ester of methacrylic acid and the polyethylene glycol ether of a C12-C22 fatty alcohol, and one or more monomers of acrylic acid, methacrylic acid, or one of their simple esters, wherein said copolymers include, but are not limited to, Acrylates/Beheneth-25 Methacrylate Copolymer and Acrylates/Steareth-20 Methacrylate Copolymer. Acrylates/Beheneth-25 Methacrylate Copolymer is commercially available from Dow Chemical, under the tradename, Aculyn™ 28. Acrylates/Steareth-20 Methacrylate Copolymer is commercially available from Dow Chemical, under the tradename, ACULYN 22.

Another acrylic- and/or acrylate-based polymer may be partially or totally crosslinked with at least one crosslinking agent. The at least one crosslinking agent can be chosen, for example, from polyunsaturated compounds, such as polyethylenically unsaturated compounds. These compounds can be chosen, for example, from polyalkenyl ethers of sucrose, polyalkenyl ethers of polyols, diallyl phthalates, divinylbenzene, allyl(meth)acrylate, ethylene glycol di(meth)acrylate, methylenebisacrylamide, trimethylolpropane tri(meth)acrylate, diallyl itaconate, diallyl fumarate, diallyl maleate, zinc (meth)acrylate, castor oil derivatives and polyol derivatives manufactured from unsaturated carboxylic acids. The at least one crosslinking agent that may also be used include, for example, unsaturated monomers comprising at least one reactive group capable of reacting with an unsaturation to form a crosslinked copolymer.

In some instances, the at least one crosslinked copolymer may, for example, be in the form of a dispersion in water. The number-average size of the copolymer particles in the dispersion generally ranges from 10 nm to 500 nm, for example, from 20 nm to 200 nm, and further, for example, from 50 nm to 150 nm. These copolymers are described, for example, in Patent Application No. WO 01/76552. For example, the crosslinked methacrylic acid/ethyl acrylate copolymer in the form of an aqueous dispersion of 30% active material manufactured and sold under the name CARBOPOL AQUA SF-1 by the company Lubrizol may be used.

The total amount of the one or more acrylic- and/or acrylate-based polymers in the leave-on hair crème may vary but is typically about 0.1 to about 10 wt. %, based on the total weight of the leave-on hair crème. The total amount of the one or more acrylic- and/or acrylate-based polymers may be about 0.1 to about 8 wt. %, about 0.1 to about 6 wt. %, about 0.1 to about 5 wt. %, about 0.5 to about 10 wt. %, about 0.5 to about 8 wt. %, about 0.5 to about 6 wt. %, about 0.5 to about 5 wt. %, based on the total weight of the leave-on hair crème.

Many nonionic surfactants are known and may be used in the leave-on hair crème. Nonetheless, in some instances, one or more nonionic surfactants may be selected from the group consisting of polyoxyalkylenated and polyglycerolated nonionic surfactants are particularly useful. For example, useful nonionic surfactants include hydrogenated castor oil (e.g., PEG-25 Hydrogenated castor oil, PEG-30 Hydrogenated castor oil, PEG-35 Hydrogenated castor oil, PEG-40 Hydrogenated castor oil, PEG-45 Hydrogenated castor oil, PEG-50 Hydrogenated castor oil, PEG-54 Hydrogenated castor oil, PEG-55 Hydrogenated castor oil, PEG-65 Hydrogenated castor oil, PEG-80 Hydrogenated castor oil, PEG-100 Hydrogenated castor oil, and PEG-200 Hydrogenated castor oil), esters of polyols with fatty acids or alkoxylated derivatives thereof (e.g., glyceryl distearate, glyceryl hydroxystearate, glyceryl laurate, glyceryl linoleate, glyceryl myristate, glyceryl oleate, glyceryl stearate, an ethoxylated derivate thereof, or a mixture thereof), and ethoxylated fatty alcohols (or $C_8$-$C_{30}$ alcohols).

In some instances, the one or more nonionic surfactants may include PEG-40 hydrogenated castor oil, oleth-5, polysorbate 80, or a mixture thereof.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

Examples of oxyalkylenated nonionic surfactants that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

As examples of polyglycerolated nonionic surfactants, polyglycerolated $C_8$-$C_{40}$ alcohols may be used. In particular, the polyglycerolated $C_8$-$C_{40}$ alcohols correspond to the following formula:

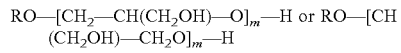

RO—[CH$_2$—CH(CH$_2$OH)—O]$_m$—H or RO—[CH(CH$_2$OH)—CH$_2$O]$_m$—H in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

The nonionic surfactant(s) may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as the compounds with the INCI names: PEG-9 to PEG-50 laurate; PEG-9 to PEG-50 palmitate; PEG-9 to PEG-50 stearate; PEG-9 to PEG-50 palmitostearate; PEG-9 to PEG-50 behenate; and the compound polyethylene glycol 100 EO monostearate (INCI name: PEG-100 stearate); and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

The sorbitol esters of $C_8$-$C_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Ubiqema.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (INCI name: Methyl glucose dioleate), the mixed ester of methylglucoside and the mixture oleic acid/hydroxystearic acid (INCI name: Methyl glucose dioleate/hydroxystearate), the ester of methylglucoside and isostearic acid (INCI name: Methyl glucose isostearate), the ester of methylglucoside and lauric acid (INCI name: Methyl glucose laurate), the mixture of monoester and diester of methylglucoside and isostearic acid (INCI name: Methyl glucose sesqui-isostearate), the mixture of monoester and diester of methylglucoside and stearic acid (INCI name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (INCI name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (INCI name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

The total amount of the one or more nonionic surfactants in the leave-on hair crème composition may vary but is typically about 1 to about 20 wt. %, based on the total weight of the leave-on hair crème. The total amount of the one or more nonionic surfactants can be about 1 to about 15 wt. %, about 1 to about 12 wt. %, about 1 to about 10 wt. %, about 2 to about 20 wt. %, about 2 to about 15 wt. %, about 2 to about 12 wt. %, about 2 to about 10 wt. %, about 4 to about 20 wt. %, about 4 to about 15 wt. %, about 4 to about 12 wt. %, about 4 to about 10 wt. %, about 5 to about 20 wt. %, about 5 to about 15 wt. %, about 5 to about 12 wt. %, or about 5 to about 10 wt. %.

Cationic polymers may be used in the leave-on hair crème of the present disclosure. Suitable examples of cationic polymers for use in the leave-on hair crème include cationic film forming polymers containing primary, secondary, tertiary and/or quaternary amine groups forming part of the polymer chain or linked directly to it and having a molecular weight of between 500 and approximately 5,000,000 and preferably between 1000 and 3,000,000.

Suitable examples of cationic polymers for use in the compositions of the present disclosure are chosen from quaternary cellulose ether derivatives, copolymers of cellulose with a water-soluble quaternary ammonium monomer, cyclopolymers, cationic polysaccharides, cationic silicone polymers, quaternized or non-quaternized vinylpyrrolidone-dialkylaminoalkyl acrylate or methacrylate copolymers, quaternary polymers of vinylpyrrolidone and of vinylimidazole, and polyaminoamides, and mixtures thereof.

Among these polymers, mention may be made more particularly of the following cationic polymers:

(1) homopolymers or copolymers derived from acrylic or methacrylic esters or amides and comprising at least one of the units of the following formulae:

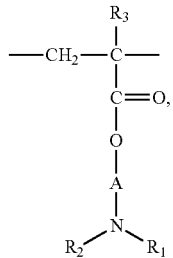

(A)

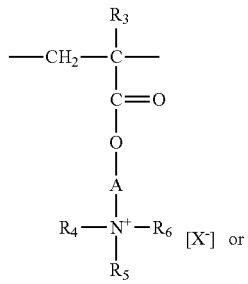

(B)

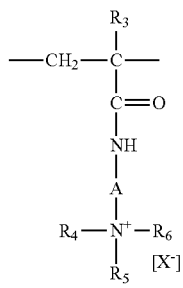

(C)

in which:

$R_3$ denotes a hydrogen atom or a $CH_3$ radical;

A is a linear or branched alkyl group comprising from 1 to 6 carbon atoms or a hydroxyalkyl group comprising from 1 to 4 carbon atoms;

$R_4$, $R_5$ and $R_6$, which may be identical or different, represent an alkyl group containing from 1 to 18 carbon atoms or a benzyl radical;

$R_1$ and $R_2$, which are identical or different, each represent a hydrogen atom or an alkyl group having from 1 to 6 carbon atoms;

X denotes a methosulfate anion or a halide such as chloride or bromide.

The copolymers of the family (1) also contain one or more units derived from comonomers that may be chosen from the family of acrylamides, methacrylamides, diacetone acrylamides, acrylamides and methacrylamides substituted on the nitrogen with lower ($C_1$-$C_4$) alkyl groups, groups derived from acrylic or methacrylic acids or esters thereof, vinyllactams such as vinylpyrrolidone or vinylcaprolactam, and vinyl esters.

Thus, among these copolymers of family (1), mention may be made of:

copolymers of acrylamide and of dimethylaminoethyl methacrylate quaternized with dimethyl sulfate or with a dimethyl halide, copolymers of acrylamide and of methacryloyloxyethyl-trimethylammonium chloride, described, for example, in patent application EP-A-080 976,
the copolymer of acrylamide and of methacryloyloxyethyltrimethylammonium methosulfate,
quaternized or non-quaternized vinylpyrrolidone/dialkylaminoalkyl acrylate or methacrylate copolymers,
polymers containing a vinylpyrrolidone unit,
dimethylaminoethyl methacrylate/vinylcaprolactam/vinylpyrrolidone terpolymers, and
quaternized vinylpyrrolidone/dimethylaminopropylmethacrylamide copolymers;

(2) non-cellulosic cationic polysaccharides, preferably containing quaternary ammonium, such as those described in U.S. Pat. Nos. 3,589,578 and 4,031,307, such as guar gums containing trialkylammonium cationic groups;

(3) quaternary copolymers of vinylpyrrolidone and of vinylimidazole;

(4) chitosans or salts thereof; the salts that can be used are, in particular, chitosan acetate, lactate, glutamate, gluconate or pyrrolidonecarboxylate;

(5) cationic cellulose derivatives such as copolymers of cellulose or of cellulose derivatives grafted with a water-soluble monomer comprising a quaternary ammonium, and described in particular in U.S. Pat. No. 4,131,576, such as hydroxyalkylcelluloses, for instance hydroxymethyl-, hydroxyethyl- or hydroxypropylcelluloses grafted in particular with a methacryloyloxyethyltrimethylammonium, methacrylamidopropyltrimethylammonium or dimethyldiallylammonium salt;

(6) polymeric quaternary ammonium salt prepared by the reaction of N-Vinyl Caprolactam (q.v.) and vinylpyrrolidone with methylvinylimidazolium methosulfate (polyquaternium-46);

(7) polymeric quaternary ammonium salt consisting of vinylpyrrolidone and quaternized imidazoline monomers (polyquaternium-44);

(8) polymeric quaternary ammonium salt formed from methylvinylimidazolium chloride and vinylpyrrolidone (polyquaternium-16);

(9) polymeric quaternary ammonium salt formed by the reaction of diethyl sulfate and a copolymer of vinyl pyrrolidone and dimethyl aminoethylmethacrylate (polyquaternium-11).

In an embodiment, the cationic polymers for use in the compositions of the present disclosure are chosen from polyquaternium-16, polyquaternium-46, polyquaternium-44, polyquaternium-11, and a mixture thereof.

The total amount of cationic polymers in the leave-on hair crème compositions can range from about 0.01 to about 5 wt. %, based on the total weight of the leave-on hair crème. In some cases, the total amount is about 0.01 to about 4 wt. %, about 0.01 to about 2 wt. %, about 0.02 to about 5 wt. %, about 0.03 to about 3 wt. %, or about 0.04 to about 2 wt. %, based on the total weight of the leave-on hair crème.

The total amount of water in the leave-on hair treatment crème may vary but is typically about 35 to about 90 wt. %, based on the total weight of the leave-on hair crème. In some cases, the total amount of water is about 40 to about 90 wt. %, about 40 to about 80 wt. %, about 50 to about 80 wt. %, or about 55 to about 75 wt. %, based on the total weight of the leave-on hair crème.

A non-limiting example of a leave-on hair crème includes:
(a) about 1 to about 30 wt. %, about 2 to about 25 wt. %, or about 5 to about 15 wt. % of one or more natural oils, for example soybean oil;

(b) about 1 to about 50 wt. %, about 5 to about 40, or about 10 to about 30 wt. % of one or more water-soluble solvents, for example, glycerin and/or caprylyl glycol;

(c) about 0.1 to about 10 wt. %, about 0.1 to about 6 wt. %, or about 0.5 to about 5 wt. % of one or more acrylic- and/or acrylate-based polymers, for example, one or more carbomers;

(d) about 1 to about 20 wt. %, or about 2 to about 15, or about 2 to about 10 wt. % of one or more emulsifiers, for example, PEG-40 hydrogenated castor oil, oleth-5, and/or polysorbate 80;

(e) optionally, about 0.01 to about 5 wt. %, about 0.01 to about 4 wt. %, or about 0.01 to about 3 wt. % of one or more cationic polymers, for example, polyquaternium-11; and (f) about 30 to about 90 wt. %, about 40 to about 80 wt. %, or about 50 to about 80 wt. % of water.

The compositions of the instant disclosure may be packaged in a variety of different containers, such as, for example, a ready-to-use container. Non-limiting examples of useful packaging include tubes, jars, caps, unit dose packages, and bottles, including squeezable tubes and bottles. The packaging may be configured so that it can be attached to a wall, such as a wall in a bathroom, including walls of a shower or tub. For example, the packaging can be a container that is configured to attach to a wall, such that when pressure is applied to the container, the composition contained therein is expelled from one or more openings in the container.

The compositions described above for use in the methods described herein may be provided in a kit. Such kits typically include at least a leave-on hair-treatment composition and a leave-on hair crème. A rinse-off conditioning mask and/or a shampoo may also optionally be included in the kit. Each of the various compositions in the kit (the leave-on hair-treatment composition, the leave-on hair crème, etc.) are typically separately contained, for example, contained in separate containers, or contained in separate compartments of packaging. Instructions, mixing components, brushes, gloves, measuring tools, etc., may also optionally be included in the kits.

Finally, as mentioned previously, the compositions and methods of the disclosure are unique in their ability to provide hair with improved manageability, and frizz control, and protection, as well as impart styling or shaping benefits to the hair. Accordingly, the instant disclosure relates to methods for treating hair, for example, for improving the manageability of hair; for imparting lasting style or shape, curl definition, and frizz control; for conditioning and/or imparting or improving ease of combability and detangling of hair. In some cases, the compositions and methods of the disclosure are used to treat curly or wavy hair. The terms "curly hair" or "wavy hair" as used herein can refer to either naturally curly or wavy hair (for example, African American hair having a certain degree of curliness) or to chemically curly or wavy hair (as subjected to waving or perming or hair chemical treatments or to relaxing/straightening chemical treatments to reduce the curliness of hair or to impart relaxing properties to hair).

Implementation of the present disclosure is provided by way of the following examples. The examples serve to illustrate the technology without being limiting in nature.

Example 1

Rinse-Off Conditioning Masks

| | INCI US | 1 | 2 | 3 | 4 | 5 | 6 |
|---|---|---|---|---|---|---|---|
| Solid Natural Fatty Compound | SHEA BUTTER | 2 | 2 | 2 | 2 | 2 | 2 |
| Natural Oil | SUNFLOWER SEED OIL | 3 | 3 | 3 | 3 | 3 | |
| | COCONUT OIL | | | | | | 3 |
| Cationic Surfactant | BEHENTRIMONIUM CHLORIDE | 2.8 | 2.8 | 2.8 | 2.8 | 2.5 | 3.5 |
| Nonionic Thickening agent | SCLEROTIUM GUM | 0.5 | 0.5 | 0.5 | 0.5 | 0.5 | 0.5 |
| Emulsifiers | CETEARYL ALCOHOL AND GLYCERYL STEARATE SE | 9 | 9 | 9 | 9 | 9 | 9 |
| Emollient | ISOPROPYL PALMITATE | 1.5 | 1.5 | 1.5 | 1.5 | 1.5 | 1.5 |
| Smectite Clay | MOROCCAN LAVA CLAY | 0.5 | 0.5 | 0.5 | | 0.5 | 0.5 |
| Water-Soluble Solvent | ISOPROPYL ALCOHOL ANDCAPRYLYL GLYCOL | 1.1 | 1.1 | 1.1 | 1.1 | 1.1 | 1.1 |
| Charcoal | CHARCOAL POWDER | | | 0.05 | | | |
| Misc. | POLYGLYCERIN COMPOUND AND DERIVATIVES | | | 0.02 | | | |
| Colorant | CARAMEL | | | | ≤1 | | |
| Misc. | FRAGRANCE, ANTI-OXIDANT PRESERVATIVES | ≤2 | ≤2 | ≤2 | ≤2 | ≤2 | ≤2 |
| Water | WATER | QS 100 | QS 100 | QS 100 | QS 100 | QS 100 | QS 100 |
| Viscosity (Rheomat) | Spindle #4 - 30 seconds @ 25° C. | 15-25 DU | 15-25 DU | 15-25 DU | 15-25 DU | 15-25 DU | 15-25 DU |

Example 2

Leave-On Hair-Treatment Compositions

| | INCI US | 7 | 8 | 9 | 10 |
|---|---|---|---|---|---|
| Solid Natural Fatty Compound | SHEA BUTTER | 3 | 3 | 3 | 3 |
| Natural Oil | COCONUT OIL | 3 | 3 | 3 | |
| | SUNFLOWER SEED OIL | | | | 3 |
| Cationic Surfactant | BEHENTRIMONIUM CHLORIDE | 0.8 | 0.8 | 0.8 | 0.8 |
| Cellulose Based Thickening Agent | HYDROXYPROPYL METHYLCELLULOSE | 0.5 | 0.5 | 0.5 | 0.5 |
| Nonionic Thickening Agent | SCLEROTIUM GUM | 0.5 | 0 | 0.5 | 0.5 |
| Emulsifiers | CETYL ESTERS AND CETEARYL ALCOHOL | 6.5 | 6.5 | 6.5 | 6.5 |
| Water Soluble Solvents | CAPRYLYL GLYCOL, GLYCERIN, AND ISOPROPYL ALCOHOL | 5.5 | 5.5 | 5.5 | 5.5 |
| Colorant | CARAMEL | | | ≤1 | |
| Misc. | FRAGRANCE, pH MODIFIER, PRESERVATIVES | ≤2 | ≤2 | ≤2 | ≤2 |
| Water | WATER | QS 100 | QS 100 | QS 100 | QS 100 |
| Viscosity (Rheomat) | Spindle #3-30 Seconds @ 25° C.* | 45-65 DU | 45-65 DU | 45-65 DU | 45-65 DU |

*a spindle #3 was used for leave-on hair treatment compositions which were less viscous than the leave-on cremes or rinse-off masks which required a spindle #4 for viscosity measurements

Example 3

Leave-On Hair Crèmes

| | INCI US | 11 | 12 | 13 | 14 |
|---|---|---|---|---|---|
| Natural Oil | SOYBEAN OIL | 9.4 | 9.4 | 9.4 | 9.4 |
| Nonionic Surfactant | PEG-40 HYDROGENATED CASTOR OIL, OLETH-5, AND/OR POLYSORBATE 80 | 6.4 | 6.4 | 6.4 | 6.4 |

-continued

| INCI US | | 11 | 12 | 13 | 14 |
|---|---|---|---|---|---|
| Acrylic- or acrylate-based polymer (Thickening Agent) | CARBOMER | 0.9 | 0.9 | 0.9 | 0.9 |
| Emollient | BIS-DIGLYCERYL POLYACYLADIPATE-2 | 0.5 | 0.5 | 0.5 | 0.5 |
| Cationic Polymer | POLYQUATERNIUM-11 | 0 | 0.08 | 0.04 | 0.08 |
| Water-Soluble Solvents | GLYCERIN AND CAPRYLYL GLYCOL | 20.3 | 10.3 | 10.3 | 10.3 |
| Misc. | COLORANTS, FRAGRANCE, NEUTRALIZING AGENT, AND PRESERVATIVE | ≤3 | ≤2 | ≤2 | ≤3 |
| | WATER | QS 100 | QS 100 | QS 100 | QS 100 |
| Viscosity (Rheomat) | Spindle #4-30 seconds @ 25° C. | 25-45 DU | 25-45 DU | 25-45 DU | 25-45 DU |

Example 4

Clinical Testing Results

Testing was carried out to determine female African American consumers' experience with a routine using compositions of Examples 1-3. The consumers had natural (non-chemically-relaxed), curly hair. The following routine was carried out:

I. Hair was shampooed with a commercially available sulfate-free shampoo.
II. After shampooing, while the hair was still damp, the rinse-off mask of Formulation #1 in Example 1 was applied to the hair. The rinse-off mask was allowed to remain on the hair for 5 minutes and then rinsed from the hair with water.
III. After the rinse-off mask was rinsed from the hair, the leave-on hair-treatment composition of Formulation #9 in Example 2 was applied to the hair.
IV. Without rinsing the leave-on hair-treatment composition (Formulation #9) from the hair, the leave-on hair crème of Formulation #11 of Example 3 was applied to the hair (to which the leave-on hair-treatment composition was already applied).
V. The hair was then dried (rollerball dried) and styled.

Consumers reported that the routine provided hair with improved curl regularity, curl definition, and discipline. Furthermore, consumers reported that after treatment with the routine, hair exhibited a noticeably improved ability to separate strands (detangling properties).

Example 5

Comparative Testing of Rinse-Off Conditioning Mask

Inventive Formulation #1 of Example 1 was tested against a commercial benchmark product (deep treatment masque).

The commercial deep treatment masque contained the following ingredients: Deionized water, *Butyrospermum Parkii* (Shea Butter), Argan Oil, Vegetable Glycerin, Emulsifying Wax, Sea Kelp Extract, Panthenol (Vitamin B-5), Essential Oil Blend, Avacado Oil, *Lonicera Caprifolium* (Honeysuckle) Flower (and) *Lonicera Japonica* (Japanese honeysuckle) Flower Extract, Tocopherol (Vitamin E), *Hyssopus Officinalis* Extract, *Salvia Officinalis* (sage) Leaf and *Equisetum Arvense* Extract, Soybean Oil, and *Daucus Carota Sativa* (Carrot) Seed Oil.

Fifteen female participants ages 18 to 55 participated in the study. The participants were Caucasian and Hispanic, and desired their hair to have a curly end-look. Participants were instructed to use either the Inventive Formulation #1 or the commercial benchmark product at least three times during a two week in-home period. After a seven day "wash out" period, the participants were instructed to use whichever product they did not use during the first week. Products were randomized to prevent bias. Participants were interviewed to assess the key attributes of the products. The findings of the study are summarized in the table below.

| Summary of Results | |
|---|---|
| Overall Preference | Most participants preferred Inventive Formulation #1 over the benchmark |
| Product Appearance | Inventive Formulation #1 was reported to appear "natural" due to the product's underlying color and the visible specks in the product |
| Ease of Use | Inventive Formulation #1 was reported to be easier to apply than the benchmark due to thickness; it distributed more evenly and adhered better to the hair; and was easier to control during application |
| Look & Feel of Wet Hair | Inventive Formulation #1 resulted in fewer knots and provided easier combing than the benchmark; it was also perceived as more moisturizing to the hair and had a "silky" feeling on the hair |
| Look & Feel of Dry Hair | Somewhat similar results between Inventive Formulation #1 and the benchmark were noted for the look and feel of dry hair. Nonetheless, Inventive Formulation #1 provided improved moisturizing to the hair compared to the benchmark |

The "earthy" appearance of Inventive Formulation #1 conveyed a sense of "naturalness" to the product, which many participants found to be quite important. Participants also that Inventive Formulation #1 was especially "user-friendly" with respect to ease of application. Also, upon rinsing the product from the hair, the participants reported that their hair was less tangled, was moisturized, and exhibited overall better cosmetic properties than with the benchmark.

Example 6

Comparative Testing of Leave-On Hair Treatment Composition

Inventive Formulation #7 of Example 2 was tested against a commercial benchmark leave-on hair treatment product.

The commercial product contained the following ingredients: Deionized Water, *Butyrospermum Parkii* (Shea Butter), *Cocos Nucifera* (Coconut) Oil, *Macadamia Ternifolia* Seed Oil, *Magnifera Indica* (Mango) Seed Butter, *Persea Gratissima* (Avacado) Oil, Vegetable Glycerin, *Aloe Barbadensis* Leaf Extract, Silk Protein, Ammonium Salt, *Melia Azadiratcha* (Neem) Seed Oil, *Daucus Carota Sativa* (Carrot) Seed oil, Sorbitol Esters, Panthenol (Pro-Vitamin B-5), Caprylyl Glycol, Essential Oil Blend, *Lonicera Caprifolium* (honeysuckle) Flower (and) *Lonicera Japonica* (Japanese Honeysuckle) Flower Extract, Tocopherol (Vitamin E), and Hibiscus Flower Extract.

Fourteen African American female participants ages 18 to 55 participated in the study. Participants were instructed to use either the Inventive Formulation #7 or the commercial benchmark product at least three times during a one week in-home period in place of their regular styling product. After a seven day "wash out" period, the participants were instructed to use whichever product they did not use during the first week for a separate one week in-home period. Products were randomized to prevent bias. Participants were interviewed to assess the key attributes of the products. The findings of the study are summarized in the table below.

| Summary of Results | |
| --- | --- |
| Hair Feel | Inventive Formulation #7 was reported to provide hair with a cleaner feeling; whereas the benchmark product was sometimes reported to have a "sticky" feeling |
| Ease of Application | Both products were found to be easy to apply to the hair |
| Hair Appearance | Inventive Formulation #7 was found to provide greater frizz control than the benchmark product, and the frizz control lasted longer; both products were found to provide defined curl properties that last from 1 to 3 days |
| Build-Up & Absorption | Both products were perceived to absorb slowly into the hair, but participants noted that their regular styling products also absorbed slowly into the hair |

Inventive Formulation #7 was found to be equivalent or better than the commercial benchmark. In particular, Inventive Formulation #7 was found to provide much better frizz control than the commercial benchmark. The commercial benchmark was reported to be "too thick" and "too sticky" by a number of participants, which were concerns not associated with Inventive Formulation #7. Nonetheless, both products provided good curl definition and were moisturizing, which participants found appealing.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

Some of the various categories of components identified may overlap. For example. In such cases where overlap may exist and the composition includes both components (or the composition includes more than two components that overlap), an overlapping compound does not represent more than one component. For example, a homopolymer of methyl quaternized dimethylaminoethyl methacrylate crosslinked by a crosslinking agent may be considered both a cationic polymer and a thickening agent. If a particular composition includes both a cationic polymer component and a thickening agent component, a single homopolymer of methyl quaternized dimethylaminoethyl methacrylate crosslinked by a crosslinking agent will serve as only the cationic polymer or only the thickening agent (the compound does not serve as both the cationic polymer and the thickening agent).

Viscosity is referred to in the units, "DU," which represents "units of deflection." The viscosity can be measured using a Rheomat 180, 108E, ER10, 200 or TVe-05 viscometer from proRheo or PCE Instruments or Lamy Technology. The viscosity measurement is generally performed from 20 to 25 degrees centigrade, wherein the Rheomat viscometer is equipped with a particular-sized spindle (e.g., No. 4), the measurement being performed after a few minutes (e.g., 10 minutes) of rotation of the spindle in a composition (after which time stabilization of the viscosity and of the spin speed of the spindle are observed), at a specified shear rate (e.g., 200 s−1).

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat" (and its grammatical variations) as used herein also refers to contacting keratinous substrates such as hair with the compositions of the present disclosure.

A "rinse-off" product refers to a composition that is rinsed and/or washed from the hair with water either after or during the application of the composition onto the hair, and before drying and/or styling the hair. At least a portion and typically the majority of the composition is removed from the hair during the rinsing and/or washing.

A "leave-on" product refers to a composition that is not rinsed and/or washed from the hair after or during application of the composition onto the hair. The composition remains on the hair during drying and/or styling.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:
1. A method for treating hair consisting of:
I. optionally, cleansing the hair;
II. optionally, treating the hair with a rinse-off conditioning mask;
III. applying a leave-on hair-treatment composition to the hair, the leave-on hair-treatment composition comprising:
(a) at least 4 wt. % of a natural fatty component, the natural fatty component comprising:
(i) one or more solid or semi-solid natural fatty compounds having a melting point of 31° C. or higher; and
(ii) one or more natural oils having a melting point below 31° C.;
wherein the weight ratio of the one or more solid or semi-solid natural fatty compounds to the one or more natural oils is about 5:1 to about 1:5;
(b) one or more cationic surfactants;
(c) one or more cellulose based thickening agents;
(d) one or more emulsifiers; and
(e) water, wherein the in the leave-on hair-treatment composition is an oil-in-water emulsion;
IV. without removing the leave-on hair-treatment composition, applying a leave-on hair créme that is different from the leave-on hair-treatment composition to the hair, the leave-on hair créme comprising:
(a) one or more natural oils;
(b) one or more water-soluble solvents;
(c) carbomers;
(d) one or more nonionic surfactants;
(e) optionally, one or more cationic polymers; and
(f) water;
V. without removing the leave-on hair-treatment composition and the leave-on hair créme, styling the hair.

2. A method of claim 1, wherein the one or more solid or semi-solid natural fatty compounds in the leave-on hair-treatment composition are selected from the group consisting of Shea butter, bayberry wax, bees wax, illipe butter, paraffin wax, hard tallow, lanolin, kokum butter, Sal butter, spermaceti, murumuru seed butter, beeswax, ceresin wax, cocoa butter, jojoba wax, candelilla wax, palm butter, carnauba wax, esparto wax, shellac wax, sugarcane wax, lignite wax, ouricouri wax, rice bran wax, castor wax, Montan wax, sugar cane wax, rice bran wax, sunflower wax, and a mixture thereof.

3. The method of claim 1, wherein the one or more solid or semi-solid natural fatty compounds in the leave-on hair-treatment composition comprises Shea butter.

4. The method of claim 1, wherein the total amount of the one or more solid or semi-solid natural fatty compounds in the leave-on hair-treatment composition is about 1 to about 10 wt. %, based on the total weight of the leave-on hair-treatment composition.

5. The method of claim 1, wherein the one or more natural oils in the leave-on hair-treatment composition are selected from the group consisting of coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a mixture thereof.

6. The method of claim 1, wherein the one or more natural oils in the leave-on hair-treatment composition comprises coconut oil.

7. The method of claim 1, wherein the total amount of the one or more natural oils in the leave-on hair-treatment composition is about 1 to about 10 wt. % based on the total weight of the leave-on hair-treatment composition.

8. The method of claim 1, wherein the leave-on hair-treatment composition comprises Shea butter as a semi-solid natural fatty compound and coconut oil as a natural oil.

9. The method of claim 1, wherein the weight ratio of the one or more solid or semi-solid natural fatty compounds to the one or more natural oils in the leave-on hair-treatment composition is about 2:1 to about 1:2.

10. The method of claim 1, wherein the one or more cationic surfactants in the leave-on hair-treatment composition are selected from the group consisting of cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethyl amine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyldiethylamine, arachidamidoethyldimethylamine, quaternium-91, and a mixture thereof.

11. The method of claim 1, wherein the total amount of the one or more cationic surfactants in the leave-on hair-treatment composition is about 0.5 to about 5 wt. %, based on the total weight of the leave-on hair-treatment composition.

12. The method of claim 1, wherein the leave-on hair-treatment composition comprises one or more cellulose based thickening agents selected from the group consisting of cellulose, carboxymethyl hydroxyethylcellulose, cellulose acetate propionate carboxylate, hydroxyethyl cellulose, hydroxyethyl ethylcellulose, hydroxypropylcellulose, hydroxypropyl methylcellulose, methyl hydroxyethylcellulose, microcrystalline cellulose, sodium cellulose sulfate, a mixtures thereof.

13. The method of claim 12, wherein the one or more cellulose based thickening agents comprises hydroxypropyl methylcellulose.

14. The method of claim 1, wherein the leave-on hair-treatment composition further includes a nonionic thickening agent that is not a cellulose-based thickening agent.

15. The method of claim 1, wherein the total amount of the one or more thickening agents in the leave-on hair-treatment composition is about 0.1 to about 8 wt. % based on the total weight of the leave-on hair-treatment composition.

16. The method of claim 1, wherein the one or more emulsifiers in the leave-on hair-treatment composition are selected from the group consisting of fatty acids, fatty alcohols, esters of polyols and of a fatty acid, polyol fatty esters and fatty ethers with a branched or unsaturated chain containing from 10 to 30 carbon atoms, esters of sorbitan and of a fatty acids, esters of sugar and of a fatty acid, and a mixture thereof.

17. The method of claim 1, wherein the total amount of the one or more emulsifiers in the leave-on hair-treatment composition is about 0.5 to about 15 wt. %, based on the total weight of the leave-on hair-treatment composition.

18. The method of claim 1, wherein the leave-on hair-treatment composition comprises:
(a) at least 4 wt. % of a natural fatty component, the natural fatty component comprising:
(i) about 1 to about 8 wt. % Shea butter; and
(ii) about 1 to about 8 wt. % of coconut oil;
wherein the weight ratio of Shea butter to coconut oil is about 2:1 to about 1:2;
(b) about 0.5 to about 5 wt. % of one or more cationic surfactants;
(c) about 0.1 to about 8 wt. % of one or more cellulose based thickening agents;
(d) about 0.1 to about 10 wt. %, of one or more emulsifiers; and
(e) about 50 to about 92 wt. % of water.

19. The method of claim 1 comprising:
II. treating the hair with a rinse-off conditioning mask by applying the rinse-off conditioning mask to the hair, allowing it to remain on the hair for a period of time, and rinsing the rinse-off conditioning mask from the hair, the rinse-off conditioning mask comprising:
(a) at least 4 wt. % of a natural fatty component, the natural fatty component comprising:
(i) one or more solid or semi-solid natural fatty compounds having a melting point of 31° C. or higher; and
(ii) one or more natural oils having a melting point below 31° C.;
wherein the weight ratio of the one or more solid or semi-solid natural fatty compounds to the one or more natural oils is about 5:1 to about 1:5;
(b) at least 1 wt. % of one or more cationic surfactants;
(c) one or more nonionic thickening agents;
(d) one or more emulsifiers;
(e) one or more mineral based clays; and
(f) water.

20. The method of claim 19, wherein the one or more solid or semi-solid natural fatty compounds in the rinse-off conditioning mask are selected from the group consisting of Shea butter, bayberry wax, bees wax, illipe butter, paraffin wax, hard tallow, lanolin, kokum butter, Sal butter, spermaceti, murumuru seed butter, beeswax, ceresin wax, cocoa butter, jojoba wax, candelilla wax, palm butter, carnauba wax, esparto wax, shellac wax, sugarcane wax, lignite wax, ouricouri wax, rice bran wax, castor wax, Montan wax, sugar cane wax, rice bran wax, sunflower wax, and a mixture thereof.

21. The method of claim 19, wherein the total amount of the one or more solid or semi-solid natural fatty compounds in the rinse-off conditioning mask is about 1 to about 10 wt. %, based on the total weight of the rinse-off conditioning mask.

22. The method of claim 19, wherein the one or more natural oils in the rinse-off conditioning mask are selected from the group consisting of coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a mixture thereof.

23. The method of claim 19, wherein the total amount of the one or more natural oils in the rinse-off conditioning mask is about 1 to about 10 wt. % based on the total weight of the rinse-off conditioning mask.

24. The method of claim 19, wherein the rinse-off conditioning mask comprises Shea butter as a semi-solid natural fatty compound and sunflower seed oil as a natural oil.

25. The method of claim 19, wherein the one or more cationic surfactants in the rinse-off conditioning mask is selected from the group consisting of cetrimonium chloride, cetrimonium methosulfate, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethyl amine, linoleamidopropyl dimethylamine, stearamidopropyl dimethylamine, isostearamidopropyl dimethyl amine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyldiethylamine, arachidamidoethyldimethylamine, quaternium-91, and a mixture thereof.

26. The method of claim 19, wherein the total amount of the one or more cationic surfactants in the rinse-off conditioning mask is at least 1 to about 10 wt. %, based on the total weight of the rinse-off conditioning mask.

27. The method of claim 19, wherein the one or more nonionic thickening agents in the rinse-off conditioning mask is selected from the group consisting of guar gum, sclerotium gum, a biopolysaccharide gum of microbial origin, gums derived from plant exudates, a cellulose based gum, a pectin, and a mixture thereof.

28. The method of claim 19, wherein the total amount of the one or more nonionic thickening agents in the rinse-off conditioning mask is about 0.1 to about 8 wt. % based on the total weight of the rinse-off conditioning mask.

29. The method of claim 19, wherein the one or more emulsifiers in the rinse-off conditioning mask are selected from the group consisting of fatty acids, fatty alcohols, esters of polyols and of a fatty acid, polyol fatty esters and fatty ethers with a branched or unsaturated chain containing from 10 to 30 carbon atoms, esters of sorbitan and of a fatty acids, esters of sugar and of a fatty acid, and a mixture thereof.

30. The method of claim 19, wherein the total amount of the one or more emulsifiers in the rinse-off conditioning mask is about 1 to about 20 wt. %, based on the total weight of the rinse-off conditioning mask.

31. The method of claim 19, wherein the one or more mineral based clays in the rinse-off conditioning mask comprises one more smectite clays.

32. The method of claim 31, wherein the one or more smectite clays are selected from the group consisting of bentonite, montmorillonite, saponite, hectorite, bidelite, stevensite, and a mixture thereof.

33. The method of claim 19, wherein the total amount of the one or more mineral based clays is about 0.1 to about 10 wt. %, based on the total weight of the rinse-off conditioning mask.

34. The method of claim 19, wherein the rinse-off conditioning mask is an oil-in-water emulsion.

35. The method of claim 19, wherein the rinse-off condition mask is allowed to remain on the hair for a period of about 1 minute to about 15 minutes before being rinsed from the hair.

36. The method of claim 19, wherein the rinse-off conditioning mask comprises:
(a) at least 4 wt. % of a natural fatty component, the natural fatty component comprising:
(i) about 1 to about 8 wt. % Shea butter; and
(ii) about 1 to about 8 wt. % of sunflower seed oil;
wherein the weight ratio of Shea butter to sunflower seed oil is about 3:1 to about 1:3;

(b) at least 1 to about 10 wt. % of one or more cationic surfactants;
(c) about 0.1 to about 8 wt. % of one or more nonionic thickening agents, wherein the one or more nonionic thickening agents comprises sclerotium gum;
(d) about 1 to about 20 wt. %, of one or more emulsifiers;
(e) about 0.1 to about 5 wt. % of a mineral based clay, wherein the one or more mineral based clays comprises a smectite clay; and
(f) about 50 to about 90 wt. % of water.

37. The method of claim 1, wherein the leave-on hair créme comprises one or more natural oils selected from the group consisting of coconut oil, wheat germ oil, sunflower seed oil, avocado oil, jojoba oil, babassu oil, macadamia oil, almond oil, apricot kernel oil, carrot oil, castor oil, citrus seed oil, corn oil, cottonseed oil, jojoba oil, linseed oil, mineral oil, mink oil, olive oil, palm kernel oil, peach kernel oil, peanut oil, rapeseed oil, safflower oil, sesame oil, soybean oil, vegetable oil, wheat germ oil, and a mixture thereof.

38. The method of claim 1, wherein the total amount of the one or more oils in the leave-on hair créme is about 1 to about 30 wt. %, based on the total weight of the leave-on hair créme.

39. The method of claim 1, wherein the leave-on hair créme comprises one or more water-soluble solvents comprise organic solvents selected from the group consisting of $C_{1-4}$ alcohols, polyols, glycols, and a mixture thereof and wherein the total amount of the one or more water-soluble solvents in the leave-on hair créme is about 1 to about 50 wt. %, based on the total weight of the leave-on hair créme.

40. The method of claim 1, wherein the one or more water-soluble solvents comprises glycerin.

41. The method of claim 1, wherein the total amount of carbomers in the leave-on hair créme is about 0.1 to about 10 wt. %, based on the total weight of the leave-on hair créme.

42. The method of claim 1, wherein the leave-on hair créme comprises one or more nonionic surfactants selected from the group consisting of polyoxyalkylenated or polyglycerolated nonionic surfactants.

43. The method of claim 42, wherein the one or more nonionic surfactants are selected from the group consisting of PEG-40 hydrogenated castor oil, oleth-5, polysorbate 80, and a mixture thereof.

44. The method of claim 1, wherein the total amount of the one or more nonionic surfactants in the leave-on hair créme composition is about 1 to about 20 wt. %, based on the total weight of the leave-on hair créme.

45. The method of claim 1, wherein the leave-on hair créme comprises one or more cationic polymers selected from the group consisting of polyquaterium-10, cetrimonium chloride, behentrimonium chloride, behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

46. The method of claim 45, wherein the one or more cationic polymers comprises polyquaternium-11.

47. The method of claim 1, wherein the leave-on hair créme comprises one or more cationic polymers in an amount of about 0.01 to about 5 wt. %, based on the total weight of the leave-on hair créme.

48. The method for treating hair of claim 1, wherein the leave-on hair-treatment composition is free of hydrolyzed wheat protein and hydrolyzed soy protein.

49. The method for treating hair of claim 1, wherein the leave-on hair créme composition is free of hydrolyzed wheat protein and hydrolyzed soy protein.

50. The method for treating hair of claim 1, wherein the leave-on hair-treatment composition and the leave-on hair créme is free of anionic thickening agents.

* * * * *